United States Patent [19]

Payne

[11] 4,148,916

[45] Apr. 10, 1979

[54] DERIVATIVES OF OXAMINIC ACIDS AND ESTERS

[75] Inventor: Trevor G. Payne, Arlesheim, Switzerland

[73] Assignee: Sandoz Ltd., Basel, Switzerland

[21] Appl. No.: 917,949

[22] Filed: Jun. 22, 1978

[30] Foreign Application Priority Data

Jun. 28, 1977 [CH] Switzerland ........................ 7913/77
Jun. 28, 1977 [CH] Switzerland ........................ 7914/77

[51] Int. Cl.$^2$ ..................... A61K 31/24; C07C 101/44
[52] U.S. Cl. .................................... 424/309; 424/319; 560/43; 562/455; 562/456
[58] Field of Search ......... 560/43; 260/518 R, 518 A, 260/519; 424/309, 319

[56] References Cited

U.S. PATENT DOCUMENTS

| 3,511,804 | 5/1970 | Duennenberger et al. ............ 560/43 |
| 3,966,965 | 6/1976 | Sellstedt et al. ..................... 424/309 |
| 4,011,337 | 3/1977 | Hall et al. ............................... 560/43 |
| 4,017,538 | 4/1977 | Hall et al. ............................. 424/309 |
| 4,061,791 | 12/1977 | Hall et al. ............................ 424/309 |
| 4,069,343 | 1/1978 | Sellstedt et al. ..................... 424/319 |

FOREIGN PATENT DOCUMENTS 2362409  6/1974  Fed. Rep. of Germany ............. 560/43

*Primary Examiner*—James O. Thomas, Jr.
*Assistant Examiner*—G. T. Breitenstein
*Attorney, Agent, or Firm*—Gerald D. Sharkin; Robert S. Honor; Timothy G. Rothwell

[57] ABSTRACT

The invention provides oxaminic acids and esters thereof, useful for the treatment of allergic conditions, a process for the preparation of said compounds and pharmaceutical compositions containing these compounds.

12 Claims, No Drawings

DERIVATIVES OF OXAMINIC ACIDS AND ESTERS

This invention relates to oxaminic acids and esters thereof, a process for the preparation of said compounds and pharmaceutical compositions containing these compounds.

More particularly, the invention provides compounds of formula I,

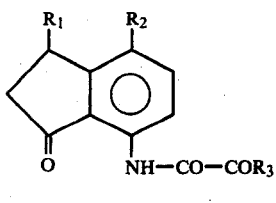

wherein
$R_1$ is hydrogen or alkyl of 1 to 10 carbon atoms,
$R_2$ is chlorine or alkoxy of 1 to 4 carbon atoms, or
$R_1$ and $R_2$ together are —$(CH_2)_m$—
wherein m is 3 or 4,
and $R_3$ is OH or alkoxy of 1 to 4 carbon atoms.

When $R_1$ is alkyl of 1 to 10 carbon atoms, this preferably contains 1 to 5 carbon atoms, especially 2 or 3 carbon atoms. $R_1$ can also be hydrogen.

$R_2$ can be chlorine. $R_2$ can also be alkoxy of 1 to 4 carbon atoms. $R_1$ and $R_2$ together can also be —$(CH_2)_m$— wherein m is 3 or 4, preferably 3.

$R_3$ can be OH. $R_3$ can also be alkoxy of 1 to 4 carbon atoms.

The invention also provides a process for the production of compounds of formula I comprising, (a) producing a compound of formula Ia,

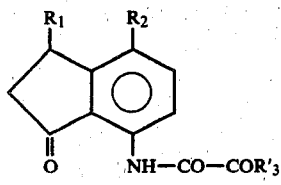

wherein $R_1$ and $R_2$ are as previously defined and
$R_3'$ is alkoxy of 1 to 4 carbon atoms, by reacting a compound of formula II,

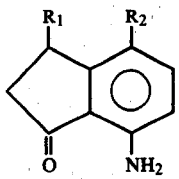

wherein $R_1$ and $R_2$ are as previously defined, with a compound of formula III, $$R_4CO-COR'_3 \qquad III$$

wherein
$R'_3$ is as previously defined and
$R_4$ is chlorine, bromine, alkoxy of 1 to 4 carbon atoms, phenoxy, or phenoxy monosubstituted by chlorine, bromine, alkyl of 1 to 4 carbon atoms or alkoxy of 1 to 4 carbon atoms, or (b) producing a compound of formula Ib,

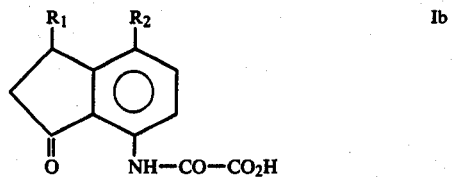

by hydrolysing a compound of formula Ia as hereinafter defined.

Process variant (a) can be effected according to known methods. For example, the reaction may conveniently be effected in the presence of an inert solvent such as a hydrocarbon, chlorinated hydrocarbon, an ether or a tertiary amine, or in an excess of the compound of formula III. The reaction may suitably be effected at a temperature of from $-5°$ to $200°$ C. A basic catalyst, such as a tertiary amine, for example pyridine or triethylamine may be employed. When $R_4$ is alkoxy of 1 to 4 carbon atoms, this preferably has the same significance as $R_3$.

Process variant (b) can be effected according to known methods. The reaction is preferably effected in the presence of a base, for example in the presence of a dilute alkali metal hydroxide or a tertiary amine. The reaction may suitably be effected at a temperature of from $0°$ C. to the boiling temperature of the reaction mixture, conveniently in the presence of an inert organic solvent which is miscible with water, such as a lower alcohol, dimethyl sulphoxide or dimethoxy ethane.

The resulting compounds of formula I may be isolated and purified using conventional techniques. The compounds of formula I wherein $R_3$ is OH may be converted into salt forms in conventional manner and vice versa. Suitable salt forms include those with alkali metals, for example sodium and potassium, alkaline earth metals, for example calcium and magnesium, and with organic bases such as amines.

The compounds of formula II can be prepared by nitrating a compound of formula IV,

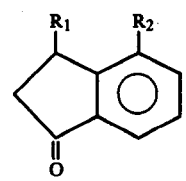

for example in a mixture of sulphuric and nitric acids, and reducing the resulting nitro derivative, according to known methods, to yield the compounds of formula II. The reduction may conveniently be effected by catalytic hydrogenation or by using iron filings in an aqueous acid.

Insofar so the production of the starting materials has not been described, these are either known or may be produced in conventional manner from available materials, or by methods analogous to those described herein.

In the following Examples, all temperatures are in degrees Celsius.

EXAMPLE 1:

N-(2,6,7,8,9,9a-hexahydro-2-oxo-1H-benz[c,d]azulen-3yl)oxaminic acid ethyl ester A solution of 5.0 g of 2,6,7,8,9,9a-hexahydro-2-oxo-1H-benz[c,d]azulen-3yl-amine in 26 ml of diethyl oxalate is refluxed for 2 hours and then cooled to room temperature. The reaction mixture is then distilled in a bulb tube at 90°–100°/11 mm to remove the excess of diethyl oxalate, and the residue is purified by chromatography on 300 g of silica gel. The title compound is recrystallised from ether, m.p. 115°–117°.

The 2,6,7,8,9,9a-hexahydro-2-oxo-1H-benz[c,d]-azulen-3yl-amine employed as starting material can be prepared as follows:

(a) A solution of 20 g of potassium nitrate in 100 ml of conc. sulphuric acid is added dropwise, with stirring, to a solution of 36 g of 2,6,7,8,9,9a-hexahydro-1H-benz[c,d]-azulen-2-one in 200 ml of conc. sulphuric acid at 5° and then stirred for 1 hour at 0°–5°. The reaction mixture is poured onto ice, extracted with chloroform, the extract washed with water, dried over sodium sulphate and concentrated. The raw product is dissolved in methylene chloride and filtered through 400 g of silica gel. After reducing the volume of the solvent, raw 2,6,7,8,9,9a-hexahydro-3-nitro-1H-benz[c,d]azulen-2-one (containing 2,6,7,8,9,9a-hexahydro-4-nitro-1H-benz[c,d]azulen-2-one) is crystallised from methanol, m.p. 107°–110°.

(b) 20 g of 2,6,7,8,9,9a-hexahydro-3-nitro-1H-benz[c,d]azulen-2-one are added to 135 ml of acetic acid and 6 g of iron filings and 18 ml of water added whilst stirring. Further charges of 6 g of iron filings and 18 ml of water are added over intervals of 15, 30, 45 and 60 minutes. The mixture is stirred for a further 30 minutes, diluted with 900 ml of water and extracted with methylene chloride. After reducing the volume of the methylene chloride extract, the remaining 2,6,7,8,9,9a-hexahydro-2-oxo-1H-benz[c,d]azulen-3yl-amine is purified by chromatography on silica gel. M.p. 135°–138°.

The following compounds can be prepared in manner analogous to that described in Example 1, using appropriate starting materials in approximately equivalent amounts.

TABLE 1

| Ex. No. | $R_1$ | $R_2$ | $R_3$ | M.P. |
|---|---|---|---|---|
| 2 | —(CH$_2$)$_3$— | | OC$_2$H$_5$ | 85°–87° |
| 3 | —(CH$_2$)$_3$— | | OCH$_3$ | 153°–155° |
| 4 | H | OCH$_3$ | OC$_2$H$_5$ | 170°–172° |
| 5 | n-C$_3$H$_7$ | Cl | OC$_2$H$_5$ | |

EXAMPLE 6:

N-(2,6,7,8,9,9a-hexahydro-2-oxo-1H-benz[c,d]azulen-3-yl) oxaminic acid

A solution of 0.95 g of potassium hydroxide in 2 ml of water is added to a solution of 4 g of the title compound of Example 1 in 150 ml of methanol and the mixture refluxed for 1 hour. The solution is concentrated, diluted with water and the neutral side products extracted with CH$_2$Cl$_2$. The aqueous phase is acidified with hydrochloric acid and the title compound filtered off. M.P. 191°–192°.

The following compounds can be prepared in manner analogous to that described in Example 5, using appropriate starting materials in approximately equivalent amounts.

TABLE 2

| Ex. No. | $R_1$ | $R_2$ | $R_3$ | M.P. |
|---|---|---|---|---|
| 7 | —(CH$_2$)$_3$— | | OH | 208°–210° |
| 8 | H | —OCH$_3$ | OH | 221°–223° |
| 9 | n-C$_3$H$_7$ | Cl | OH | |

The compounds of formula I possess pharmacological activity. In particular, the compounds possess disodium chromoglycate (DSCG)-like activity, and are therefore useful in the treatment and prophylaxis of allergic conditions, such as allergic asthma, exercise-induced asthma and allergic gastro-intestinal disorders, as indicated in the passive cutaneous anaphylaxis (PCA) test in the rat.

The method employed is based on those described by Mota (1), Stotland and Share (2) and Perper et al. (3). Female rats (180–200 g) are sensitized by subcutaneous administration of 1 mg of ovalbumin (Fluka No. 05430) and 200 mg of aluminum hydroxide gel (Merck No. 1088), dissolved in 1 ml of 0.9% saline, and intraperitoneal administration of 0.5 ml of Haemophilus pertussis vaccine (Schweizerisches Serum- und Impfinstitut, Bern, No. 115,325; 4×10$^{10}$ organism/ml). Fourteen days later, the animals are exsanguinated, the blood centrifuged and the serum (anti-serum) collected and deep frozen.

(1) Mota, I., Immunology 7, 681 (1964).
(2) Stotland, M. and Share, N. N., Can. J. Physiol. Pharmacol. 52, 1114 (1974).
(3) Perper, R. J., Oronsky, A. L. and Blancuzzi, V., J. Allergy Clin. Immunol. 53, 66 (1974).

The anti-serum is injected intradermally (0.1 ml of a 1:100 to 1:200 dilution per injection site) at three sites on the backs of untreated, female rats. Twenty-four hours later (intravenous testing) or forty-eight hours later (oral testing), the rats receive either solvent or the test compound (2 ml/kg i.v., 0.1 to 3.2 mg/kg i.v. or 5 ml/kg p.o., 1 to 32 mg/kg p.o.) followed one minute (intravenous testing), or 7.5 or 15 minutes (oral testing) later by the intradermal injection or histamine (8 μg in 0.05 ml of 0.9% saline) and serotonin (0.5 μg in 0.05 ml of 0.9% saline) at two further sites. Immediately afterwards, the animals receive an intravenous injection of 1 ml of a 0.9% saline solution containing 5 mg of ovalbumin (twice crystallised) and 2.5 mg of Evans blue dye. The ovalbumin, histamine and serotonin elicit a cutaneous anaphylactic/anaphylactoid reaction, the intensity of which is proportional to the distance to which the dye diffuses into the tissue surrounding the seven sensitisation sites. Thirty minutes later, the rats are killed by CO$_2$ inhalation and the diameter in mm of the blue spot at each anti-serum, histamine and serotonin injection site measured. The drug dose decreasing the diameter of the blue area by 50% compared with solvent pretreated control rats (ED50), is obtained from the regression line. The dose-effect correlation is tested for statistical significance.

The DSCG-like activity, in particular histamine release inhibitor activity, can be confirmed by inhibition of histamine release in the passive peritoneal analphylaxis test in the rat.

Rats are passively sensitised by intraperitoneal injection of 3 ml of 1:2 to 1:10 diluted rat anti-ovalbumin serum. Twenty-four hours later, the rats are trested intravenously (0.1 to 3.2 mg/kg i.v.) with the test compound. Immediately after intravenous application, the anaphylactic reaction is elicited by intravenous administration of 1 ml of 0.5% ovalbumin, immediately followed by 5 ml of HBSS (Hank's balanced salt solution) intraperitoneally. Five minutes later, the animals are decapitated and the peritoneal fluid collected and kept in an ice bath. After centrifugation for 5 minutes (350 g) at 4° C., the histamine content of the supernatant liquid is estimated fluorophotometrically (4). The effects of the test compounds are expressed as percentage changes in histamine release compared with controls.

(4) Kusner, E. J. and Herzig, D. J., In: Advances in Automated Analysis, vol. II, Thurman Associates, Maimi (1971).

For the above-mentioned use, the dosage will, of course, vary depending on the compound used, mode of administration and therapy desired. However, in general, satisfactory results are obtained when administered at a daily dosage of from about 0.015 to about 100 mg/kg of animal body weight, conveniently given in divided doses 2 to 4 times a day or in sustained release form. For the larger mammal, the total daily dosage is in the range of from about 1 to about 100 mg, and dosage forms suitable for oral administration comprise from about 0.25 to about 50 mg of the compounds admixed with a solid or liquid pharmaceutical carrier or diluent.

The compounds of formula I wherein $R_3$ is OH may be administered in free form or in pharmaceutically acceptable salt form. Such salt forms possess the same order of activity as the free forms and are readily prepared in conventional manner. Examples of suitable salt forms are those of sodium and potassium.

The invention also provides a pharmaceutical composition comprising a compound of formula I and, in the case of compounds wherein $R_3$ is OH, in free form or in pharmaceutically acceptable salt form, in association with a pharmaceutically acceptable diluent or carrier. Such compositions may, for example, be in the form of a solution or capsule.

What we claim is:

1. A compound of formula

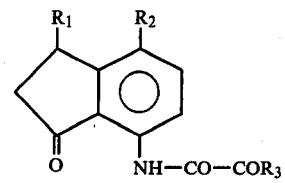

I wherein
$R_1$ is hydrogen or alkyl of 1 to 10 carbon atoms,
$R_2$ is chlorine or alkoxy of 1 to 4 carbon atoms, or
$R_1$ and $R_2$ together are —$(CH_2)_m$—, wherein m is 3 or 4,
and $R_3$ is OH or alkoxy of 1 to 4 carbon atoms, and, in the case of compounds wherein $R_3$ is OH, in free form or in pharmaceutically acceptable salt form.

2. A compound of claim 1, wherein $R_1$ and $R_2$ together are —$(CH_2)_3$— and $R_3$ is $OC_2H_5$.

3. A compound of claim 1, wherein $R_1$ and $R_2$ together are —$(CH_2)_3$— and $R_3$ is $OCH_3$.

4. A compound of claim 1, wherein $R_1$ is H, $R_2$ is OMe and $R_3$ is $OC_2H_5$.

5. A compound of claim 1, wherein $R_1$ and $R_2$ together are —$(CH_2)_3$— and $R_3$ is OH.

6. A compound of claim 1, wherein $R_1$ is H, $R_2$ is OMe and $R_3$ is OH.

7. A compound of claim 1, wherein $R_3$ is OH.

8. A compound of claim 1, wherein $R_3$ is alkoxy of 1 to 4 carbon atoms.

9. N-(2,6,7,8,9,9a-hexahydro-2-oxo-1H-benz[c,d,]azulen-3yl)oxaminic acid ethyl ester.

10. N-(2,6,7,8,9,9a-hexahydro-2-oxo-1H-benz[c,d]azulen-3yl)oxaminic acid.

11. A pharmaceutical composition comprising an antihistamine responsive amount of a compound of claim 1 to relieve allergic conditions, in association with a pharmaceutically acceptable diluent or carrier.

12. A method of treating antihistamine responsive allergic conditions in animals, which comprises administering to an animal in need of such treatment, an effective amount of a compound of claim 1.

* * * * *